US00PP25039P3

(12) United States Plant Patent
Danziger

(10) Patent No.: US PP25,039 P3
(45) Date of Patent: Nov. 4, 2014

(54) ***CLEOME* PLANT NAMED 'DCLEO2'**

(50) Latin Name: ***Cleome* hybrid**
Varietal Denomination: DCLEO2

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 13/986,008

(22) Filed: Mar. 22, 2013

(65) Prior Publication Data

US 2014/0289923 P1 Sep. 25, 2014

(51) Int. Cl.
*A01H 5/00* (2006.01)

(52) U.S. Cl.
USPC ..... Plt./416

(58) Field of Classification Search
USPC ..... Plt./416
See application file for complete search history.

*Primary Examiner* — June Hwu
*Assistant Examiner* — Keith Robinson
(74) *Attorney, Agent, or Firm* — Cassandra Bright

(57) ABSTRACT

A new and distinct *Cleome* cultivar named 'DCLEO2' is disclosed, characterized by a long and continuous blooming season. Plants are strong, upright, with excellent branching, and foliage that is dark and not typically sticky. The new variety has very compact and mounded habit and short peduncles. The new variety is a *Cleome*, normally produced as an outdoor garden or container plant.

2 Drawing Sheets

Figure 1:
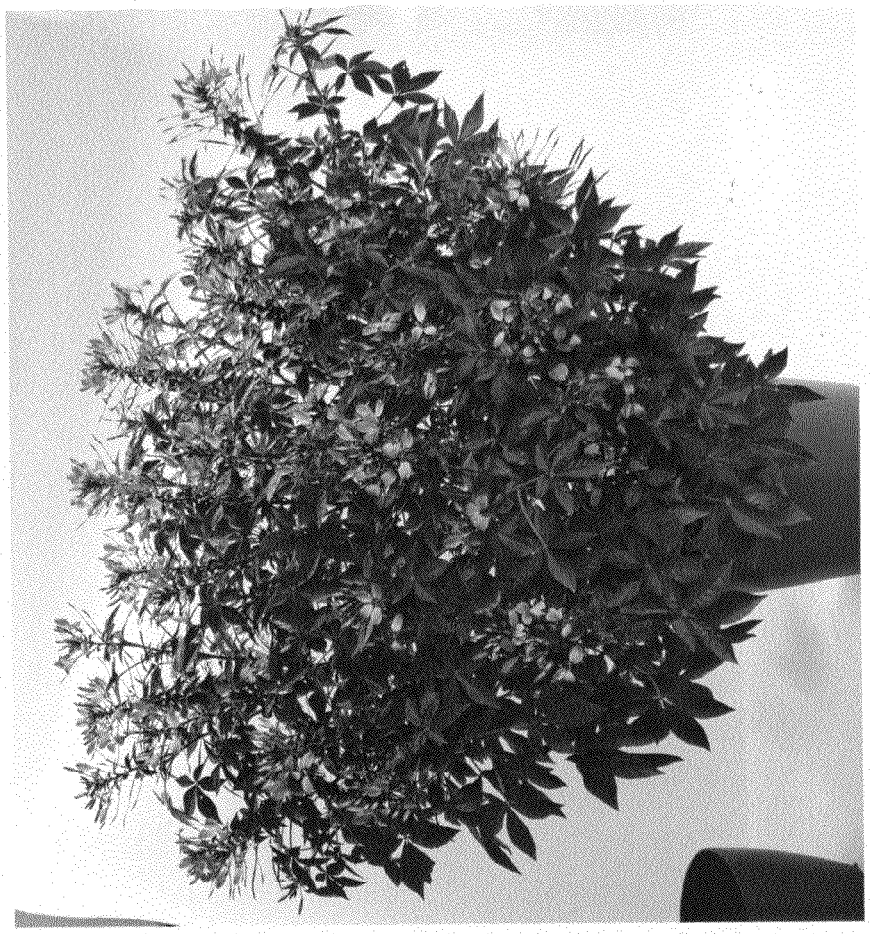

Latin name of the genus and species: *Cleome* hybrid.
Variety denomination: 'DCLEO2'.

BACKGROUND OF THE INVENTION

The new *Cleome* cultivar is a product of a planned breeding program conducted by the inventor, Gavriel Danziger, in Moshav Mishmar Hashiva, Israel. The objective of the breeding program was to produce new *Cleome* varieties for ornamental commercial applications. The open pollination resulting in this new variety was made during October of 2009.

The seed parent is the unpatented, proprietary seedling variety referred to as *Cleome* hybrid 'CM-Z-1'. The pollen parent is unknown as it was an open pollination breeding program. The new variety was discovered in June of 2010 by the inventor in a group of seedlings resulting from the 2009 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in February of 2011 and has shown that the unique features of this cultivar are stable and reproduced true to type in more than 100 successive generations.

SUMMARY OF THE INVENTION

The cultivar 'DCLEO2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCLEO2' These characteristics in combination distinguish 'DCLEO2' as a new and distinct *Cleome* cultivar:

1. Strong, upright plant habit.
2. Very good branching with approximately 20 branches per plant.
3. Distinctive dark foliage.
4. Exceptionally long flowering season
5. Continuous flowering.
6. Leaves that lack typical sticky texture of *Cleome.*
7. Very strong garden performance.
8. Sterile flowers Plants of the new cultivar 'DCLEO2' are similar to plants of the seed parent, *Cleome* hybrid 'CM-Z-1' in most horticultural characteristics, however, plants of the new cultivar 'DCLEO2' are less compact than the seed parent. Additionally 'DCLEO2' produces a larger flower with a longer pedicel than the seed parent.

COMMERCIAL COMPARISON

Plants of the new cultivar 'DCLEO2' are comparable to the variety *Cleome* 'INNCLEOSR', U.S. Plant Pat. No. 19,733. The two *Cleome* varieties are similar in most horticultural characteristics; however, plants of the new variety 'DCLEO2' are less compact produce larger flowers, with longer pedicels. Additionally, 'DCLEO2' produces foliage with more leaflet, and of a different color than that of the comparator.

Plants of the new cultivar 'DCLEO2' are comparable to the variety *Cleome* 'Robspivio', U.S. Plant Pat. No. 15,969. The two *Cleome* varieties are similar in most horticultural characteristics; however, the new variety 'DCLEO2' differs in producing smaller, sterile flowers. Additionally, foliage of the new variety is darker than foliage of this comparator.

BRIEF DESCRIPTION OF THE PHOTOGRAPHS

The accompanying photograph in FIG. 1 illustrates in full color a typical plant of 'DCLEO2' grown in a greenhouse, in a 12 cm pot. Age of the plant photographed is approximately 24 weeks from a rooted cutting.

Figure 2:
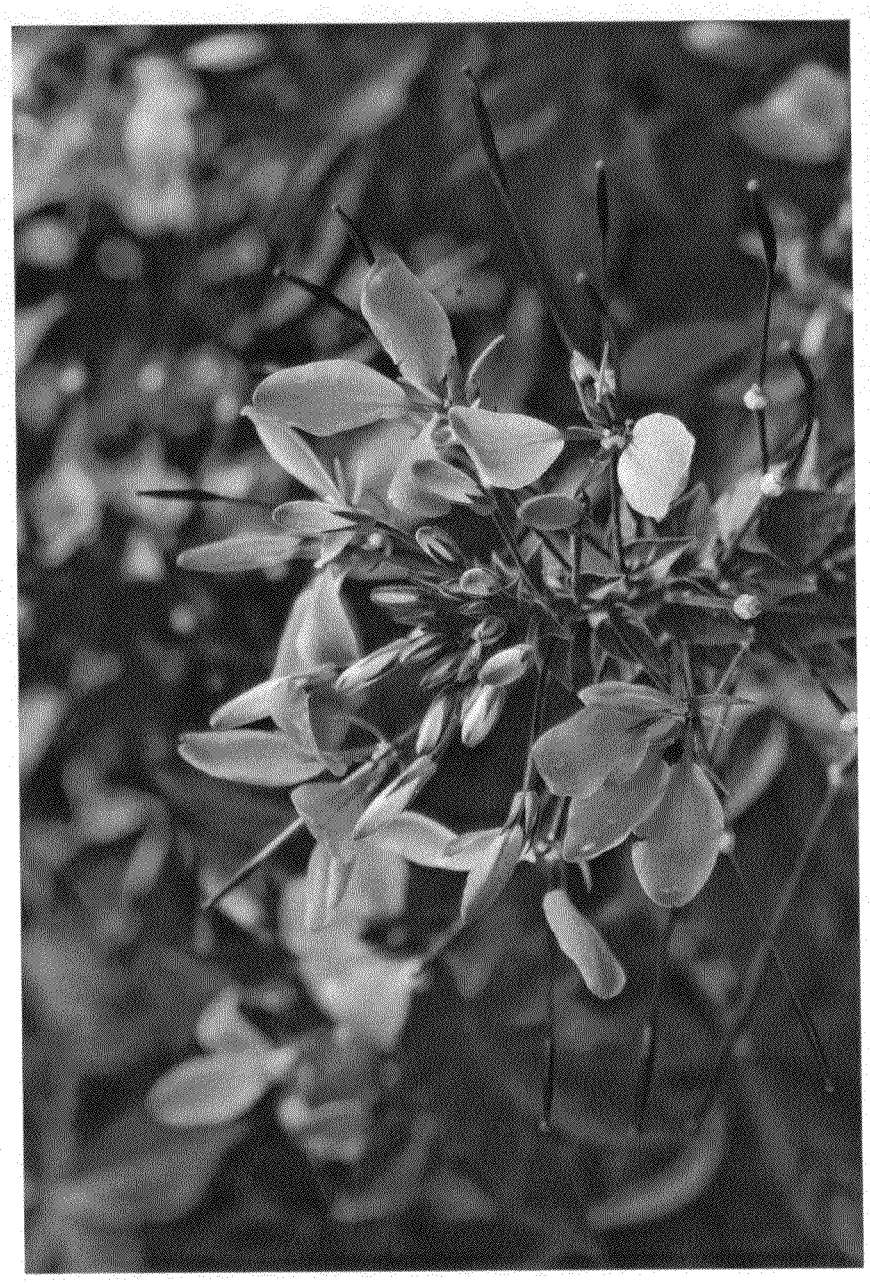

FIG. 2 illustrates in full color a close up of a typical bloom of 'DCLEO2'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'DCLEO2' plants grown outdoors during March through August in Moshav Mishmar Hashiva, Israel. The growing temperature ranged from 18° C. to 28° C. during the day and from 13° C. to 18° C. during the night. General light conditions are bright, normal sunlight. Measurements and numerical values represent averages of typical plant types.
Botanical classification: *Cleome* hybrid 'DCLEO2'.

PROPAGATION

Time to initiate roots: About 8-15 days at approximately 16-27° C.
Time to produce a rooted cutting: About 14-20 days at 16-27° C.
Root description: Fibrous, branching.

PLANT

Age of plant described: Approximately 12 weeks from rooted cutting.
Plant habit: Upright, freely branching.
Height: Approximately 50 cm.
Plant spread: Approximately 35 cm.
Growth rate: Vigorous, fast growing.
Primary stem:
- *Color*.—Near RHS 144A.
- *Texture/pubescence*.—Canescent.
- *Average length*.—Approximately 50 cm. (mature plant can get to 0.9 m).
- *Average width*.—Approximately 0.5 cm.

Branching characteristics: Freely branching with approximately 20 branches per plant.
Internode length: Approximately 4 cm.
Age of plant described: Approximately 7 weeks from a rooted cutting.

FOLIAGE

Leaf:
- *Quantity per plant*.—240 Average.
- *Average leaf length*.—Approximately 6 cm (young leaf 5 cm, mature leaf 7 cm).
- *Average leaf width*.—Approximately 7 cm.
- *Overall leaf blade shape*.—Digitate.
- *Leaf aspect*.—Slight upward cupping.
- *Angle of attachment*.—Obtuse angle to stem.

Leaflets:
- *Average leaflets per leaf*.—5.
- *Average leaflet length*.—Approximately 5-7 cm.
- *Average leaflet width*.—Approximately 2 cm.
- *Leaflet shape*.—Elliptic.
- *Leaflet apex*.—Acute.
- *Leaflet base*.—Cuneate.
- *Margin*.—Entire.
- *Aspect*.—Flat.
- *Texture of top surface*.—Puberulous.
- *Texture of bottom surface*.—Puberulous.
- *Color*.—Young foliage upper side: Near R.H.S. Green 137B. Young foliage under side: Near R.H.S. Green 137C. Mature foliage upper side: Near R.H.S. Green 137A. Mature foliage under side: Near R.H.S. Green 137B.

Venation:
- *Type*.—Pinnate.
- *Venation coloration upper side*.—Near R.H.S. Green 137B.
- *Venation coloration under side*.—Near R.H.S. Green 137C.

Leaflet petiole (if present):
- *Length*.—Approximately 0.4 cm.
- *Width*.—1.5 mm.
- *Color*.—Near RHS Yellow-Green 146C.
- *Strength*.—Strong.
- *Texture*.—Pubescent, all surfaces.

Petiole:
- *Average length*.—Approximately 7 cm.
- *Diameter*.—Approximately 1.5 mm.
- *Color*.—Near RHS Yellow-Green 144B.

FLOWER

Natural flowering season: Spring-Summer.
Inflorescence type and habit: Single flowers (with bilateral symmetry) arranged in terminal racemes. Freely flowering habit, with about 10 open flowers and about 30 flower buds per raceme.
Flower longevity on plant: 4 days.
Quantity of flowers: About 240 buds and 60 fully opened flowers per plant.
Inflorescence size:
- *Diameter*.—Approximately 8.5 cm.
- *Height*.—Approximately 15-18 cm.
- *Individual flowers per inflorescence*.—Average 10 fully open and 30 buds.

Individual flower size:
- *Diameter*.—Approximately 4 cm.
- *Height*.—Approximately 2.5 cm.

Petals:
- *Petal quantity*.—4 per flower.
- *Petal arrangement*.—Single whorl.
- *Margin*.—Entire.
- *Tip shape*.—Obtuse, broadly acute.
- *Length*.—2 cm.
- *Width*.—0.8 cm.
- *Petal apex shape*.—Broadly acute.
- *Texture*.—Smooth, glabrous.

Color:
- *Petals*.—When opening: Upper surface: Near RHS Purple 77B. Lower surface: Near RHS Purple N78D. Fully opened: Upper surface: Towards the apex near RHS Purple N78B, The base of the petals near RHS N78C. Lower surface: Near RHS Purple N78C.

Bud:
- *Shape*.—Lanceolate.
- *Length*.—1.5 cm.
- *Diameter*.—4 mm.
- *Color*.—Near RHS Purple N78C.

Sepals:
- *Shape*.—Quantity per flower: 4.
- *Length*.—Approximately 0.5 cm.

*Width*.—Approximately 1 mm.
*Margin*.—Entire.
*Texture*.—Smooth, Glabrous.
*Color*.—Near RHS Yellow-Green 146B.

Peduncle:
*Length*.—7-10 cm.
*Diameter*.—2-3 mm.
*Color*.—Near RHS Yellow-Green 144A.
*Orientation*.—Upright to 30° from vertical.
*Strength*.—Strong, flexible.

Pedicel:
*Length*.—2-2.5 cm.
*Diameter*.—Less than 1 mm.
*Color*.—Near RHS Greyed-Purple N186C.
*Orientation*.—Between 45° to 90°.
*Strength*.—Flexible.

REPRODUCTIVE ORGANS

Stamens:
*Number*.—6.
*Filament length*.—Approximately 2.5 mm.

Anthers:
*Shape*.—Acicular, Elliptic.
*Length*.—Approximately 0.4-0.5 cm.
*Color*.—Near RHS Yellow-Orange 22A.
*Pollen*.—None observed.

Pistil:
*Number*.—1 per flower.
*Length*.—Approximately 0.8-2 cm depends on the flower age.
*Style*.—Length: Approximately less than 1 mm. Color: Near RHS Greyed-Purple N187C.
*Stigma*.—Shape: Rounded. Color: Near RHS Greyed-Purple N186D. Ovary color: Near RHS Greyed-Purple N186C.
*Additional structure*.—Between the Ovary and the receptacle there is a stalk like structure — length 2-2.5 cm, 0.2 cm diameter and colored near RHS Greyed-Purple N186C.

OTHER CHARACTERISTICS

Drought tolerance and cold tolerance: Tolerant of hot, humid summer climates. Low temperature tolerance to at least 10 degree C., and high temperature tolerance to at least 40 degree C.

Fruit/seed production: Not observed.

Resistance/susceptibility to diseases and pests: Not observed to date.

What is claimed is:

1. A new and distinct cultivar of *Cleome* plant named 'DCLEO2' as herein illustrated and described.

* * * * *